US012065927B2

(12) United States Patent
Muharrag (10) Patent No.: US 12,065,927 B2
(45) Date of Patent: Aug. 20, 2024

(54) DRAINAGE BOTTLE APPARATUS FOR SATURATED ROCK PLUG SAMPLES

(71) Applicant: SAUDI ARABIAN OIL COMPANY, Dhahran (SA)

(72) Inventor: Jaber Ibrahim Muharrag, Dammam (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 302 days.

(21) Appl. No.: 17/648,456

(22) Filed: Jan. 20, 2022

(65) Prior Publication Data

US 2023/0228190 A1 Jul. 20, 2023

(51) Int. Cl.
*G01N 33/24* (2006.01)
*E21B 49/08* (2006.01)
*G01N 1/20* (2006.01)
*G01N 1/40* (2006.01)

(52) U.S. Cl.
CPC ......... *E21B 49/081* (2013.01); *G01N 1/2035* (2013.01); *G01N 1/4077* (2013.01); *G01N 2001/2071* (2013.01); *G01N 2001/4088* (2013.01); *G01N 33/24* (2013.01)

(58) Field of Classification Search
CPC .... G01N 1/2035; G01N 1/4077; G01N 33/24; E21B 49/081
See application file for complete search history.

(56) References Cited

U.S. PATENT DOCUMENTS 4,936,335 A * 6/1990 Macon .................... B01F 25/10
137/268
5,490,545 A 2/1996 Sokoloff et al.

FOREIGN PATENT DOCUMENTS

GB 739485 A 11/1955
KR 20210058776 A 5/2021

* cited by examiner

*Primary Examiner* — Jamel E Williams
(74) *Attorney, Agent, or Firm* — Osha Bergman Watanabe & Burton LLP (57) ABSTRACT

A drainage bottle apparatus includes a cylindrical body portion with a base, a neck portion, a receptor opening located at a rim, a first and a second threaded inner perimeter surface, a removable sieve having a sieve outer perimeter rim thread, and a sieve base. The sieve outer perimeter rim thread mates with the second threaded inner perimeter surface. A method for extracting a rock plug sample includes using the drainage bottle apparatus in combination with a sample jar containing a rock plug sample and a liquid material. The sample jar includes a sample jar outer perimeter surface thread that mates with the first threaded inner perimeter surface of the neck portion and is turned over so as to drain the liquid material thereby separating the liquid material from the rock plug sample and the rock plug sample, now dried, may be extracted.

19 Claims, 5 Drawing Sheets

DRAINAGE BOTTLE APPARATUS FOR SATURATED ROCK PLUG SAMPLES

BACKGROUND

In the petroleum industry, hydrocarbons are located in reservoirs far beneath the Earth's surface. Wells are drilled into these reservoirs to access and produce the hydrocarbons. Wells are structures that include casing strings, cement, and various production equipment. As a wellbore is created beneath the Earth's surface, rock plug samples or rock core samples are often brought to Earth's surface for examination. A rock plug sample is a cylindrical section of rock that is drilled and removed from the path of the wellbore. This rock plug sample is often saturated in oil, brine, or other liquids when collected and stored in a sample jar, until examination. The rock plug sample is examined to determine a variety of rock characteristics relevant to hydrocarbon exploration including porosity, permeability, or presence of hydrocarbon material.

To accurately examine a rock plug or rock core sample, it must be dried from the liquid it is saturated in. Removing the saturated rock plug sample from the sample jar so that it can dry can be a hazardous process as the samples are often saturated in dark oil making the rock plug sample difficult to locate and slippery to handle with tongs or other equipment. Once the rock plug sample is removed and dried it may be examined more accurately. The rock characteristics determined from the rock plug sample may aid in drilling decisions.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments disclosed herein relate to a drainage bottle apparatus. The drainage bottle apparatus comprises a cylindrical body portion with a base, a neck portion, a receptor opening located at a rim, a first and a second threaded inner perimeter surface, a removable sieve having a sieve outer perimeter rim thread and a sieve base, wherein the sieve outer perimeter rim thread mates with the second threaded inner perimeter surface. The drainage bottle apparatus is used in combination with a sample jar containing a rock plug sample and a liquid material in order to extract a rock plug sample. The sample jar comprises a sample jar outer perimeter surface thread that mates with the first threaded inner perimeter surface of the neck portion and is turned over so as to drain the liquid material thereby separating the liquid material from the rock plug sample and the rock plug sample, now dried, may be extracted.

In general, in one aspect, embodiments disclosed herein relate to a method to extract a rock plug sample. A drainage bottle, comprising a cylindrical body portion with a base, a neck portion, a receptor opening located at a rim, a first and a second threaded inner perimeter surface a removable sieve having a sieve outer perimeter rim thread and a sieve base, wherein the sieve outer perimeter rim thread mates with the second threaded inner perimeter surface, is used in combination with a sample jar containing a rock plug sample and a liquid material. The sample jar comprises a sample jar outer perimeter surface thread that mates with the first threaded inner perimeter surface of the neck portion and is turned over so as to drain the liquid material thereby separating the liquid material from the rock plug sample and the rock plug sample, now dried, may be extracted.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

The embodiments disclosed herein describe a drainage bottle apparatus and a method to extract a rock plug sample. During a drilling operation, rock plug samples are often collected for examination. The samples are often saturated in oil, brine, or other liquids when collected and stored in a sample jar, until examination. The embodiments disclosed herein describe a drainage bottle apparatus equipped with a removable sieve, that may be used in connection with, a sample jar, to drain the liquid from a sample jar, dry out a rock plug sample, and provide an easy means of rock plug sample extraction. The method to use the drainage bottle apparatus is also disclosed herein. A drainage bottle apparatus with a removable sieve connected, is attached to the opening of a sample jar, containing the rock plug sample and liquid material, creating a single rock plug sample drainage piece. The apparatus is turned upside down to allow for the liquid to transfer from the sample jar into the drainage bottle apparatus. The removable sieve allows for the liquid material to pass, while holding the rock plug sample into place. The sample jar is then removed from the single rock plug sample piece and the rock plug sample is extracted. The apparatus used in combination with the method described, provides for an efficient, quick and safe method to extract a rock plug sample that is submerged in a liquid material without risk of spillage, or damaging the sample.

Figure 1:
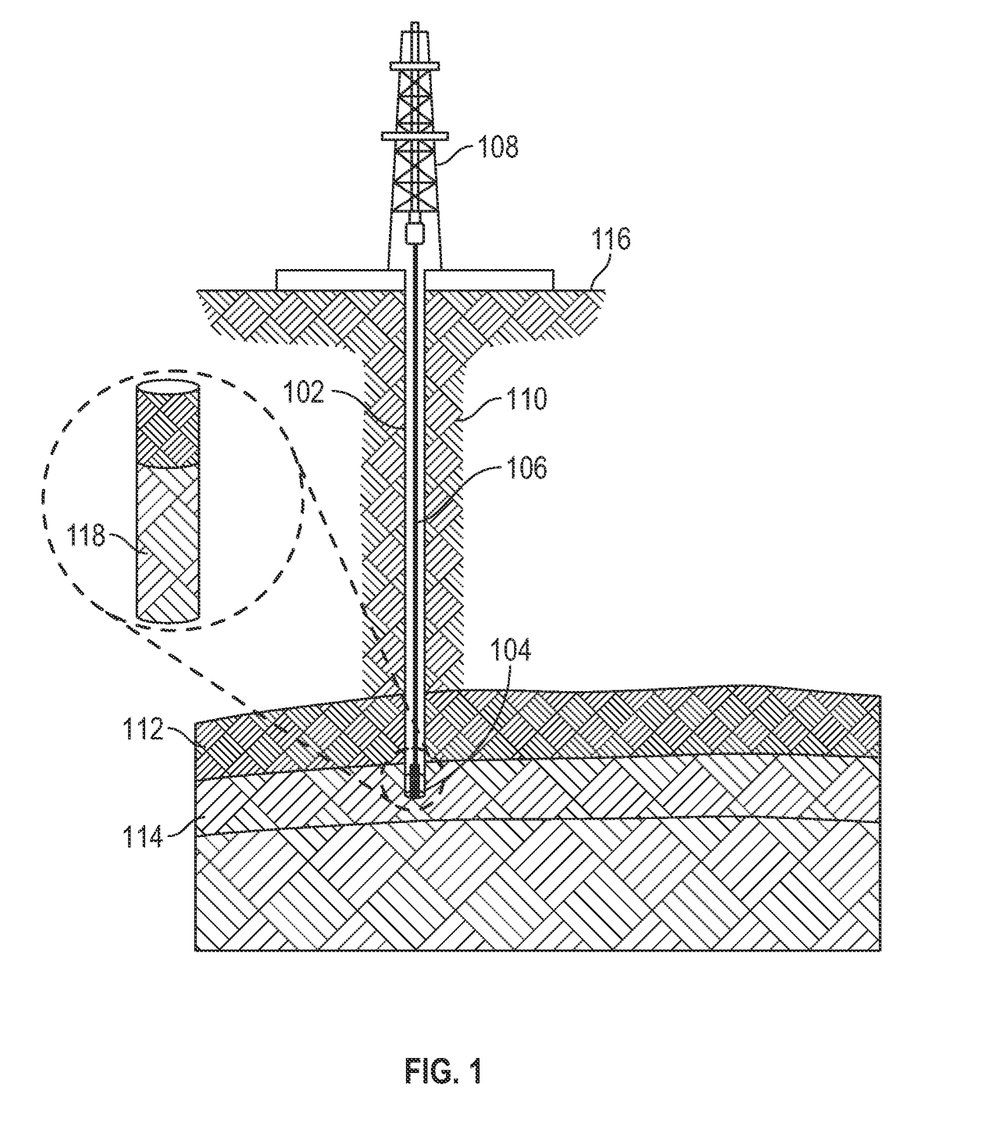
FIG. 1 shows a system in accordance with one or more embodiments.

FIG. 1 illustrates a drilling operation in accordance with one or more embodiments. As shown in FIG. 1, a well (102) may be drilled by a drill bit (104) attached by a drill pipe (106) to a drill rig (108) located on the Earth's surface (116). The well (102) may traverse a plurality of overburden layers (110) and one or more cap-rock layers (112) to a hydrocarbon reservoir (114). Throughout the drilling process, a rock plug sample (118) may be collected and sent to Earth's surface (116) to be examined to aid in drilling decisions. The rock plug sample (118) may be examined to determine characteristics relevant to hydrocarbon exploration including porosity, permeability, or presence of hydrocarbon material. The rock plug sample is stored in a sample jar, until examination. In order for the rock plug sample (118) to be examined accurately, the rock plug sample (118) must be dried and stored safely.

Figure 2:
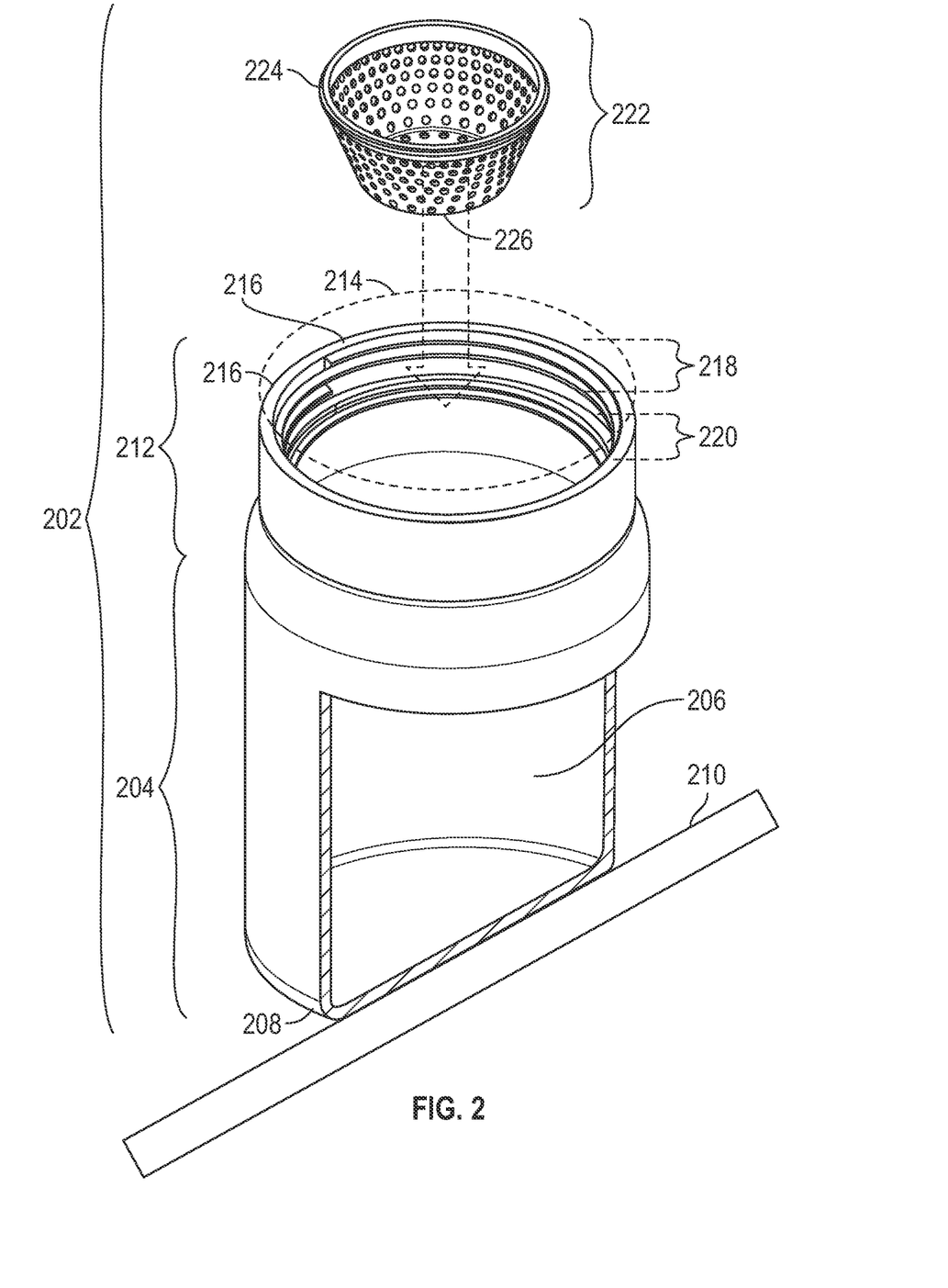
FIG. 2 shows an apparatus in accordance with one or more embodiments.

FIG. 2 shows a drainage bottle apparatus (202) in accordance with one or more embodiments. The following description of the drainage bottle apparatus (202) will be describing the apparatus while it is in an active position. The different positions the apparatus may be used in, will be described in more detail with FIGS. 4A-4C. This drainage bottle apparatus (202) comprising an oil and water compatible material, including glass or plastic, is specifically designed for efficiently, quickly, and safely extracting a rock plug sample that is submerged in oil, brine, or some other liquid from inside a sample jar while draining the liquid material from the rock plug sample, drying the rock plug sample in the process. In accordance with one or more embodiments, the drainage bottle apparatus (202) comprises a cylindrical body portion (204) with a hollow inner portion (206) meant to house the liquid material to be drained, closed by a base (208).

The base (208) of the drainage bottle apparatus (202) is a bottom structural support volume that contacts a horizontal support surface (210). The base (208) will be in contact with the horizontal support surface (210) when the drainage bottle apparatus (202) is in an active position.

The drainage bottle apparatus (202) further comprises a neck portion (212) extending from the cylindrical body portion (204) to a receptor opening (214) located at a rim (216) of the neck portion (212). A first threaded inner perimeter surface (218) and a second threaded inner perimeter surface (220) are disposed within the neck portion (212). The first threaded inner perimeter surface (218) is located directly under the rim (216) of the neck portion (212) on the hollow inner portion (206) of the drainage bottle apparatus (202). The second threaded inner perimeter surface (220) is located directly under the first threaded inner perimeter surface (218).

The neck portion (212) has a diameter that is equal to the cylindrical body portion (204) where the neck portion (212) extends away from the cylindrical body portion (204) and a diameter that is less that the cylindrical body portion (204) where the neck portion (212) ends at the rim (216) that surrounds the receptor opening (214). The dimensions of the drainage bottle apparatus (202) will be discussed in more detail at the conclusion of the FIG. 2 description.

The drainage bottle apparatus (202) further comprises a removable sieve (222) having a sieve outer perimeter rim thread (224) and a sieve base (226). The removable sieve (222) comprises a metal or a similar hard material, so that it may withstand the weight of a rock plug sample and prolonged usage. The removable sieve is considered an inclusion of the drainage bottle apparatus (202) and is the only portion comprising a metal or similar hard material. The remainder of the drainage bottle apparatus (202) comprises an oil and water compatible material, including glass or plastic. The removable sieve (222) may be attached as a component of the drainage bottle apparatus (202) when the device is in an active position or removed from the drainage bottle apparatus (202) to be cleaned when not in use. The ability to clean the removable sieve (222) will help with the durability of the device, particularly in circumstances where the liquid material being drained contains corrosive liquids.

The removable sieve (222) is attached to the drainage bottle apparatus (202) by mating the sieve outer perimeter rim thread (224) with the second threaded inner perimeter surface (220) that is disposed within the neck portion (212). Mating the threaded surfaces together describes rotating the removable sieve (222) so that the sieve outer perimeter rim thread (224) screws into the second threaded inner perimeter surface (220) until it locks into place and can no longer be rotated. This action is similar to screwing a cap onto a lid.

In accordance with one or more embodiments, the following dimensions for the drainage bottle apparatus (202) are given to be able to seamlessly mate with a sample jar having a height of 12 cm (centimeters), a mouth having a diameter of 5.2 cm and a sample jar base diameter of 7 cm. Although the previous dimensions describe the typical sample jar used in the oil industry, those skilled in the art will readily appreciate that many modifications including different dimensions are possible without materially departing from this invention. The drainage bottle apparatus (202), in order to seamlessly mate with the sample jar, comprises a height of 12 cm, a receptor opening (214) diameter of 5.7 cm, a diameter of the including, a base (208) diameter of 7 cm, a neck portion (212) height of 2.8 cm, and a rim (216) of the neck portion (212) thickness of 0.24 cm. The drainage bottle apparatus has a diameter of 6.5 cm when measuring from the rim (216) of the neck portion (212). The removable sieve (222) has a height of 2.7 cm, a sieve base (226) diameter of 3.5 cm, a sieve outer perimeter rim thread (224) diameter of 5.5 cm and thickness of 0.3 cm and openings of the removable sieve (222) having a 0.02 cm diameter to allow for liquid to drain through.

Figure 3:
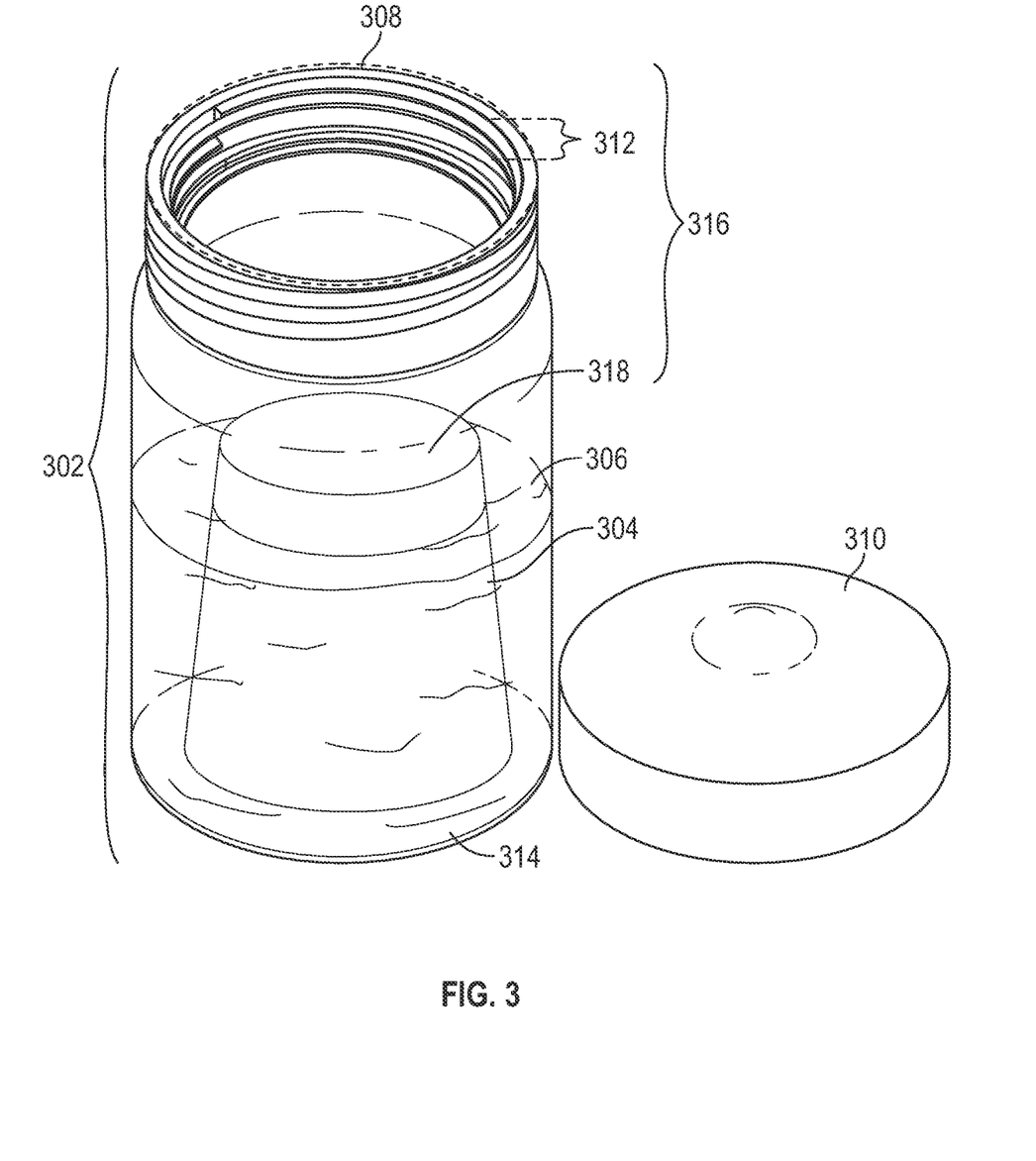
FIG. 3 shows an apparatus in accordance with one or more embodiments.

FIG. 3 shows a sample jar (302) containing a rock plug sample (304) submerged in a liquid material (306). When a rock plug sample (304) is collected from a wellsite, it is common practice is to store the rock plug sample (304) inside a sample jar (302) having a height of 12 cm with a mouth (308) having an opening diameter of 5.2 cm. Although the previous dimensions describe the typical sample jar (302) used in the oil industry, those skilled in the art will readily appreciate that many modifications including different dimensions are possible in the example embodiments without materially departing from this invention.

A sample jar (302) includes a sample jar lid (310) to contain the rock plug sample (304). A sample jar lid (310) should remain on the sample jar (302) until ready for the rock plug sample (304) drainage and retrieval. When the drainage bottle apparatus is ready for use and has the removable sieve component connected, the sample jar lid (310) should be removed, exposing the mouth (308) that is an opening to the sample jar (302) with a rock plug sample (304) and a liquid material (306) inside the sample jar (302). The end surface of the rock plug sample (304) that is the closest to the mouth (308) is referred to as the rock plug sample sieve contact surface (318). FIG. 3 shows the sample jar lid (310) in its removed state. Further descriptions of the sample jar (302) will be referring to the sample jar (302) having a sample jar lid (310) removed.

The sample jar (302) has a sample jar base (314) providing bottom structural support and contacts a horizontal support surface when the drainage bottle apparatus is in an inactive position. The sample jar (302) has a mouth (308) that has a diameter that is less than the diameter of the receptor opening of the drainage bottle apparatus, so that the receptor opening of the drainage bottle apparatus may act as a port for receiving a sample jar (302). The sample jar (302) has a sample jar outer perimeter surface thread (312) located on an outer neck surface (316) that mates with the first threaded inner perimeter surface disposed within the neck portion of the drainage bottle apparatus. Mating these threaded surfaces together describes rotating the drainage bottle apparatus so that the first threaded inner perimeter surface screws into the sample jar outer perimeter surface thread (312) until it locks into place and can no longer be rotated creating an airtight connection.

Figure 4A:
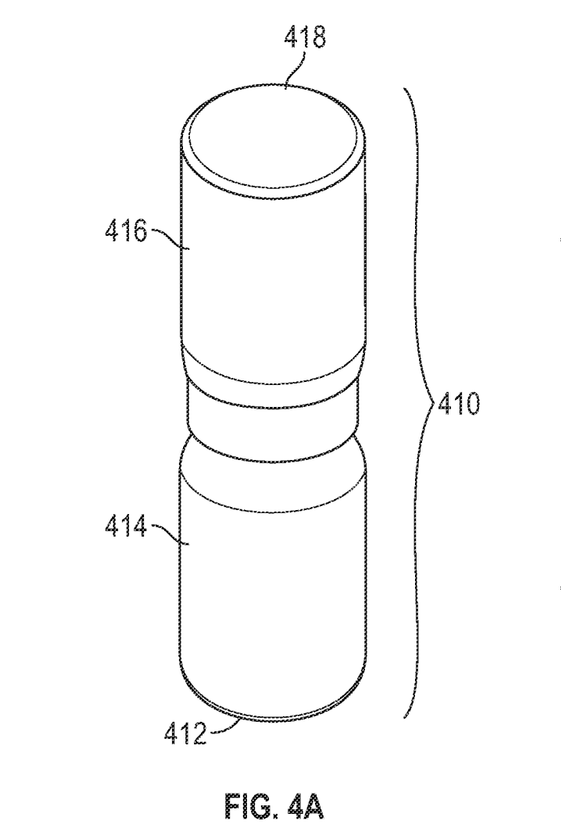
FIGS. 4A-4C shows an apparatus in active use in accordance with one or more embodiments.
Figures 4B, 4C:
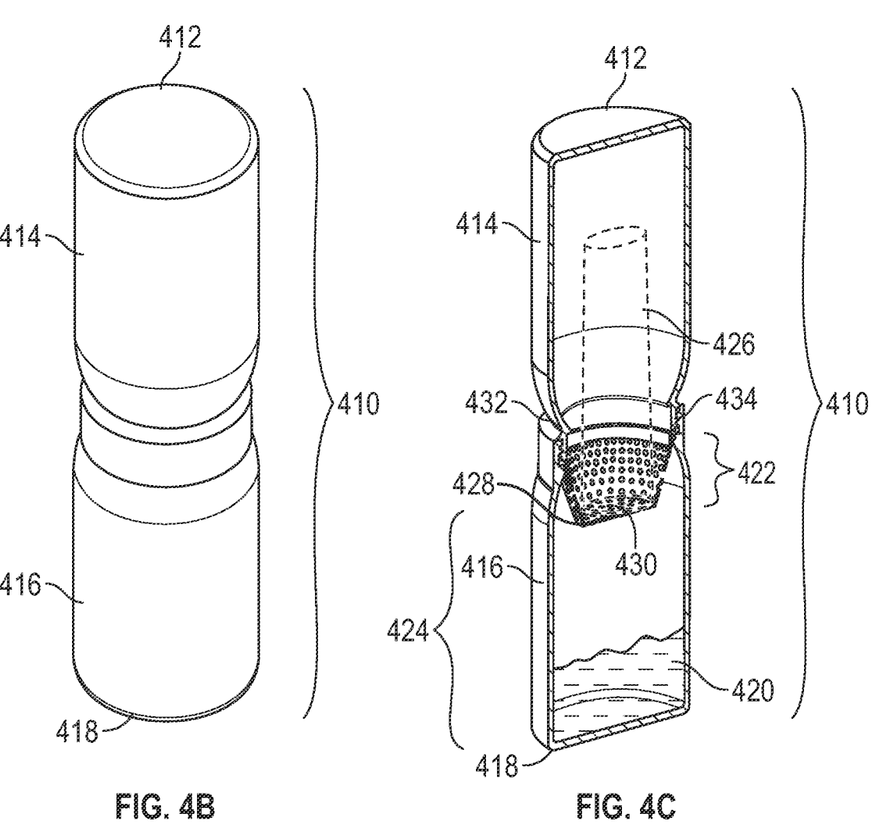

FIGS. 4A-4C shows the connections between a drainage bottle apparatus and a sample jar in accordance with one or more embodiments. To properly mate the drainage bottle apparatus to a sample jar, the drainage bottle apparatus, with the removable sieve attached, is picked up off the ground such that the receptor opening of the drainage bottle apparatus surrounds the mouth of the sample jar. The sample jar and the drainage bottle apparatus become threadedly mated by screwing the first threaded perimeter surface into the sample jar outer perimeter surface thread until locked in place. When the drainage bottle apparatus is securely threadedly mated to the sample jar, a single rock plug sample drainage piece is created.

FIG. 4A shows a single rock plug sample drainage piece (410) in an inactive position in accordance with one or more embodiments. The inactive position describes the single rock plug sample drainage piece (410) when a sample jar base (412) from the sample jar (414) is providing bottom structural support for the single rock plug sample drainage piece (410) and contacts a horizontal support surface. The drainage bottle apparatus (416) with the removable sieve securely connected is threadedly mated to the sample jar (414) and has a base (418) that does not contact a horizontal support surface. Not shown in FIG. 4A is a rock plug sample and a liquid material contained within the sample jar portion. The single rock plug sample may only need to remain in an inactive position until all the threaded mated connections are checked to be secure.

Once the single rock plug sample has been secured in the inactive position, it is turned over to an active position, so as to drain the liquid material through the removable sieve into the cylindrical body portion thereby separating the liquid material form the rock plug sample. The rock plug sample, cylindrical in shape, fits onto the sieve base, when turned over to an active position. The sieve base provides a horizontal support surface for a rock plug sample sieve contact surface when the apparatus is in active use. The sieve base is designed with a base dimension that fits the standard rock plug sample base sieve contact surface.

FIG. 4B shows a single rock plug sample drainage piece (410) in an active position in accordance with one or more embodiments. In an active position, the base (418) of the drainage bottle apparatus (416) is providing bottom structural support for the single rock plug sample drainage piece (410) and is contacting a horizontal support surface. The sample jar (414) now has a sample jar base (412) that does not contact a horizontal support surface.

FIG. 4C shows a section through a single rock plug sample drainage piece (410) in the active position in accordance with one or more embodiments. A liquid material (420) is shown collected at the base (418) of the drainage bottle apparatus (416). This liquid material (420) has passed from the sample jar (414) through removable sieve (422) into the cylindrical body portion (424) of the drainage bottle apparatus (416). The rock plug sample (426) is standing upright, with a rock plug sample sieve contact surface (428) making horizontal contact with a sieve base (430). The threaded connection between sample jar (414) and the drainage bottle apparatus (416) where a first threaded inner perimeter surface disposed in a neck portion of the drainage bottle apparatus (416) is threaded with the sample jar outer perimeter surface thread, is shown at location (432). Location (434) shows a threaded connection between the sieve outer perimeter rim thread and the second threaded inner perimeter surface.

Figure 5:
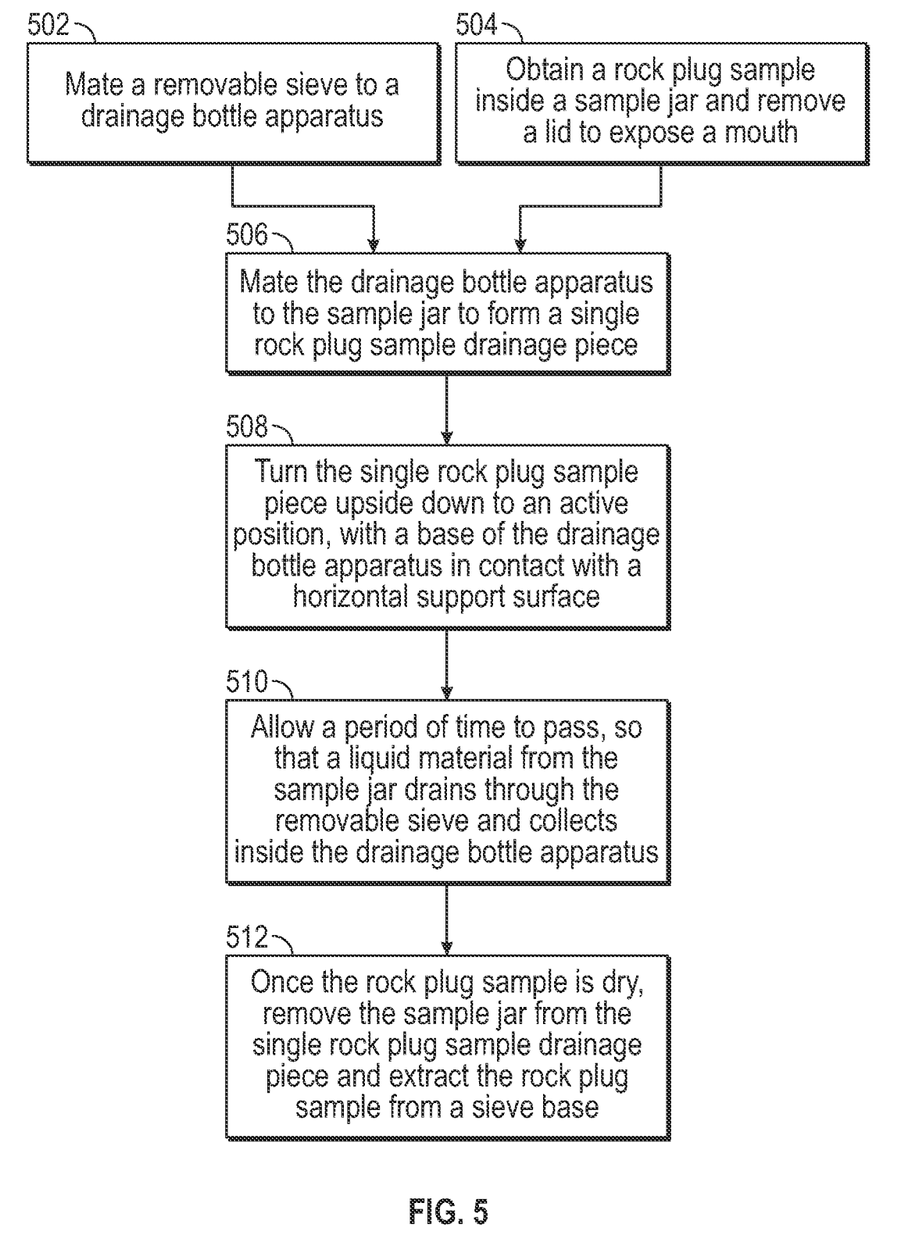
FIG. 5 shows a flowchart in accordance with one or more embodiments.

FIG. 5 shows a flowchart describing the method for efficiently, quickly, and safely extracting a rock plug sample that is submerged in oil, brine, or some other liquid from inside a sample jar. In Step 502, in accordance with one or more embodiments, a removable sieve is mated to a drainage bottle apparatus. The removable sieve is inserted inside the drainage bottle apparatus with a sieve base passing through a receptor opening first and a sieve outer perimeter rim thread passing through the receptor opening last. The removable sieve is attached by mating the sieve outer perimeter rim thread with the second threaded inner perimeter surface. Mating the threaded surfaces together describes rotating the removable sieve so that the sieve outer perimeter rim thread screws into the second threaded inner perimeter surface until it locks into place and can no longer by rotated creating an airtight connection. The removable sieve should always be mated with the drainage bottle apparatus when being used.

In Step 504, in accordance with one or more embodiments, a rock plug sample inside a sample jar is obtained and the lid is removed to expose a mouth of the jar containing the rock plug sample. The sample jar is the standard jar used to collect rock plug samples. The sample jar may then be placed on a horizontal support surface such as a table, with the sample jar base in contact with the horizontal support surface and remain in contact with the horizontal support surface throughout Step 506.

In Step 506, in accordance with one or more embodiments, the drainage bottle apparatus is mated to the sample jar to form a single rock plug sample drainage piece. This is accomplished by picking up the drainage bottle apparatus off a horizontal support surface, such that the receptor opening of the drainage bottle apparatus surrounds the mouth of the sample jar. The sample jar and the drainage bottle apparatus become threadedly mated by screwing the first threaded perimeter surface into the sample jar outer perimeter surface thread until locked in place creating an airtight connection. When the drainage bottle apparatus is securely threadedly mated to the sample jar, a single rock plug sample drainage piece is created in an inactive position. The position is labeled an "inactive position" because the rock plug sample is still contained in the original sample jar and is still submerged in a liquid material. The single rock plug sample drainage piece is illustrated in FIG. 4A.

In Step 508, in accordance with one or more embodiments, the single rock plug sample piece is then turned upside down to an active position, with a base of the drainage bottle apparatus in contact with a horizontal support surface, illustrated in FIGS. 4B-4C. When the single rock plug sample piece is turned upside down, the rock plug sample sieve contact surface will slide into contact with the sieve base and be held upright inside the removable sieve, while the liquid material drains through the openings of the removable sieve into the cylindrical body portion of the drainage bottle apparatus. With the threaded connections locked in place, the single rock plug sample piece has an airtight connection allowing for a drainage process to continue with no spillage. The position is labeled an "active position" because the apparatus is actively draining the liquid material from the sample jar and drying the rock plug sample at the same time.

In Step 510, in accordance with one or more embodiments, a period of time should be allowed for the liquid material from the sample jar to drain through the holes of the removable sieve and collect inside the cylindrical body portion of the rock plug sample drainage piece. After A minimum of 30 seconds after all the liquid material has completely drained from the sample jar, the rock plug sample is ready for extraction. The sample jar, which is standard for industry practices, is a clear glass which makes it easily recognizable when all the liquid material has been drained from inside.

Once the rock plug sample has been drying for a period of time, the sample jar is removed from the single rock plug sample piece and the rock plug sample is extracted from the sieve base, in accordance with Step 512. The sample jar is removed from the single rock plug piece by unscrewing the sample jar outer perimeter surface thread from the first threaded inner perimeter surface. The sample jar now removed may be placed aside. The rock plug sample is now extracted from the sieve base and may be examined. The rock plug sample is usually extracted by tongs, or by hand. If the rock plug sample is removed by hand, proper PPE should be worn including gloves. The rock plug sample at this point in the process is dried and easily retrievable without the risk of spilling liquid material.

If the rock plug sample were attempted to be retrieved directly from the sample jar at Step 504, the rock plug sample could be damaged by poor handling due to limited visibility from the liquid materials contained inside the sample jar. Risk of spillage would also be higher as no liquid material has been drained and the rock plug sample is still saturated in the liquid material. The method described herein, using the drainage bottle apparatus and a sample jar to create a single rock plug sample piece, provides an efficient, quick, and safe method to extract a rock plug sample submerged in a liquid material and draining out that liquid material without the risk of spillage or damage to the samples.

Although only a few example embodiments have been described in detail above, those skilled in the art will readily appreciate that many modifications are possible, including dimensions, in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed is:

1. A drainage bottle apparatus comprising:
    a cylindrical body portion with a base;
    a neck portion extending from the cylindrical body portion to a receptor opening located at a rim of the neck portion,
    wherein the neck portion further comprises an oil and water compatible material, including glass or plastic and having a diameter that is equal to the cylindrical body portion of the drainage bottle apparatus where the neck portion extends away from the cylindrical body portion and less than the cylindrical body portion, where the neck portion ends at the rim that surrounds the receptor opening,
    wherein a first threaded inner perimeter surface and a second threaded inner perimeter surface are disposed within the neck portion;
    a removable sieve having a sieve outer perimeter rim thread and a sieve base, wherein the sieve outer perimeter rim thread mates with the second threaded inner perimeter surface of the neck portion;
    a sample jar having a sample jar outer perimeter surface thread,
    wherein the sample jar outer perimeter surface thread mates with the first threaded inner perimeter surface of the neck portion; and
    a sample jar base,
    wherein the sample jar base provides bottom structural support and contacts a horizontal support surface when the drainage bottle apparatus is in an inactive position,
    wherein the sample jar contains a rock plug sample and a liquid material, and
    wherein, when the sample jar and the removable sieve are threadedly mated with the neck portion, the drainage bottle apparatus can be turned over so as to drain the liquid material through the removable sieve into the cylindrical body portion thereby separating the liquid material from the rock plug sample.

2. The apparatus of claim 1, wherein the cylindrical body portion further comprises an oil and water compatible material, including glass or plastic and a hollow inner portion, meant to house the liquid material to be drained.

3. The apparatus of claim 2, wherein the hollow inner portion is closed by a base, comprising the oil and water compatible material, which is a bottom structural support volume that contacts a horizontal support surface when the drainage bottle apparatus is standing up in an active position.

4. The apparatus of claim 1, wherein the receptor opening is a port for receiving a sample jar with a mouth having a diameter that is less than the diameter of the receptor opening.

5. The apparatus of claim 4, wherein the sample jar further comprises having a sample jar lid removed, exposing the mouth with a rock plug sample and a liquid material inside the sample jar.

6. The apparatus of claim 1, wherein the first threaded inner perimeter surface is located directly under the rim of the neck portion on a hollow inner portion of the drainage bottle apparatus and mates with the sample jar outer perimeter surface thread.

7. The apparatus of claim 1, wherein the second threaded inner perimeter surface is located directly under the first threaded inner perimeter surface and mates with the sieve outer perimeter rim thread of the removable sieve.

8. The apparatus of claim 1, wherein the removable sieve comprises of metal or a similar hard material and having the sieve base providing the horizontal support surface for a rock plug sample sieve contact surface when the drainage bottle apparatus is in an active position.

9. A method for extracting a rock plug sample, the method comprising:
obtaining the rock plug sample inside a sample jar and removing a sample jar lid to expose a mouth;
mating a removable sieve to a drainage bottle apparatus;
mating the drainage bottle apparatus to the sample jar to form a single rock plug sample drainage piece;
turning the single rock plug sample drainage piece upside down to an active position, having a base of the drainage bottle apparatus in contact with a horizontal support surface;
allowing for a period of time to pass, draining a liquid material from the sample jar through the removable sieve and collecting the liquid material inside the drainage bottle apparatus; and
removing the sample jar from the single rock plug sample drainage piece and extracting the rock plug sample from a sieve base.

10. The method of claim 9, wherein the mouth of the sample jar further comprises a sample jar outer perimeter surface thread located on an outer neck surface.

11. The method of claim 9, wherein mating the removable sieve to the drainage bottle apparatus further comprises inserting the removable sieve inside the drainage bottle apparatus with the sieve base passing through a receptor opening first and a sieve outer perimeter rim thread passing through the receptor opening last.

12. The method of claim 11, wherein mating the removable sieve inside the drainage bottle apparatus further comprises screwing the sieve outer perimeter rim thread into a second threaded inner perimeter surface of the drainage bottle apparatus.

13. The method of claim 12, wherein the second threaded inner perimeter surface is located directly under a first threaded inner perimeter surface disposed within a neck portion of the drainage bottle apparatus.

14. The method of claim 9, wherein mating the drainage bottle apparatus to the sample jar to form the single rock plug sample drainage piece further comprises inserting the drainage bottle apparatus having a receptor opening facing the mouth of the sample jar with a sample jar base in contact with the horizontal support surface and screwing a first threaded inner perimeter surface of the drainage bottle apparatus onto a sample jar outer perimeter surface thread of the sample jar.

15. The method of claim 14, wherein the first threaded inner perimeter surface is located directly under a rim of a neck portion on a hollow inner portion of the drainage bottle apparatus.

16. The method of claim 14, wherein the single rock plug sample drainage piece comprises an airtight connection allowing for a drainage process that transfers a liquid material from the sample jar into the drainage bottle apparatus, without spillage, when turning the single rock plug sample drainage piece to an active position.

17. The method of claim 16, wherein turning the single rock plug sample drainage piece to the active position moves a rock plug sample sieve contact surface into contact with a sieve base, providing a horizontal support surface for a rock plug sample and allowing the rock plug sample to be held upright inside a removable sieve.

18. The method of claim 9, wherein the period of time to pass is a minimum of 30 seconds after all of the liquid material drains through the removable sieve and collects inside the drainage bottle apparatus.

19. The method of claim 9, wherein removing the sample jar from the single rock plug sample drainage piece further comprises unscrewing a sample jar outer perimeter surface thread from a first threaded inner perimeter surfaces and removing the rock plug sample from the sieve base comprises using tongs or retrieving with gloves if by hand.

* * * * *